(12) United States Patent
Downey et al.

(10) Patent No.: US 6,254,538 B1
(45) Date of Patent: Jul. 3, 2001

(54) SYSTEM AND PROCESS FOR PERFORMING PERCUTANEOUS BIOPSY WITHIN THE BREAST USING THREE-DIMENSIONAL ULTRASONOGRAPHY

(75) Inventors: Donal B. Downey; Aaron Fenster, both of London (CA)

(73) Assignee: Life Imaging Systems, Inc. (CA)

( * ) Notice: Subject to any disclaimer, the term of this patent is extended or adjusted under 35 U.S.C. 154(b) by 0 days.

(21) Appl. No.: 09/242,112

(22) PCT Filed: Aug. 15, 1997

(86) PCT No.: PCT/CA97/00572

§ 371 Date: Apr. 29, 1999

§ 102(e) Date: Apr. 29, 1999

(87) PCT Pub. No.: WO98/06334

PCT Pub. Date: Feb. 19, 1998

Related U.S. Application Data (60) Provisional application No. 60/023,975, filed on Aug. 15, 1996.

(51) Int. Cl.[7] .................................................. A61B 8/00
(52) U.S. Cl. ......................... 600/439; 128/915; 128/916
(58) Field of Search ..................................... 600/439, 437, 600/471, 407, 567, 572; 378/37; 178/915–916

(56) References Cited

U.S. PATENT DOCUMENTS

| | | | | |
|---|---|---|---|---|
| 4,433,690 | * | 2/1984 | Green et al. ........................... | 128/915 |
| 5,479,927 | * | 1/1996 | Shmulewitz ...................... | 128/915 X |
| 5,647,373 | * | 7/1997 | Paltieli ................................. | 600/567 |
| 5,660,185 | * | 8/1997 | Shmulewitz et al. ............ | 600/437 X |
| 5,776,062 | * | 7/1998 | Nields .............................. | 128/916 X |
| 5,820,552 | * | 10/1998 | Crosby et al. .................... | 600/439 X |
| 5,833,627 | * | 11/1998 | Shmulewitz et al. ................ | 600/562 |

* cited by examiner

*Primary Examiner*—Francis J. Jaworski
(74) *Attorney, Agent, or Firm*—Katten Muchin Zavis (57) ABSTRACT

A system and process are provided for performing percutaneous biopsy within a breast using three-dimension ultrasonography and including a breast positioning device, a breast immobilization device, an ultrasonic imaging device, a biopsy instrument positioning device, the breast immobilization device and the three-dimensional ultrasonographic imaging device being positioned in a known relationship to each other, the breast immobilization device being employed to immobilize the breast and a lesion contained therein for imaging by the three-dimensional ultrasonic imaging device, and the three-dimensional ultrasonic imaging device being employed to assist an operator in positioning the biopsy instrument positioning device relative to the lesion and guiding a biopsy instrument percutaneously to the lesion.

13 Claims, 6 Drawing Sheets

SYSTEM AND PROCESS FOR PERFORMING PERCUTANEOUS BIOPSY WITHIN THE BREAST USING THREE-DIMENSIONAL ULTRASONOGRAPHY

This appln. is a 371 of PCT/CA 97/00572 filed Aug. 15, 1997 and also claims benefit of Provisional No. 60/023,975 filed Aug. 15, 1996.

BACKGROUND OF THE INVENTION

1. Field of the Invention

The present invention relates to percutaneous medical procedures within the breast. More specifically, the present invention relates to a system and process for performing percutaneous biopsy and instrument guidance within the breast under the imaging and guidance of two-dimensional and/or three-dimensional ultrasonography.

2. Description of the Prior Art

Breast cancer poses a serious threat to the lives of Canadian women. According to the American Cancer Society, one in nine North American women will develop mammary carcinoma (American Cancer Society 1992). This figure has increased from one in twenty in 1940 and reflects a steadily increasing incidence of breast cancer over the last few decades. Breast cancer has shown the highest occurrence of all female cancers, and was the second highest cause of cancer death for women in 1990 and 1991 (Amer. Cancer Soc. 1991). For women aged between 35 and 54, breast cancer is the leading cause of death (Beatty 1992). In 1994, an estimated 17,000 breast cancers were detected in Canadian women, and 5,400 Canadian women died of this disease (NCIC 1994).

Historically, breast disease has been detected and diagnosed using x-ray mammography. Mammography is not only widely available and relatively inexpensive, it has also generally been regarded to be the most sensitive single test available for breast cancer, with a detection rate of 90–95 percent (Frankl 1988, Castor, 1987, Moskowitz 1983, Baker 1982). Early detection and diagnosis have been shown to improve both the morbidity and mortality rates from breast cancer (Shapiro 1982, Morrison 1989, Tabar 1990). Diagnosis of detected focal abnormalities using mammography is based on morphological features of breast lesions such as boundary appearance and distribution of calcifications. Although some lesions can be specifically characterized in this way as either benign or malignant, a large number are radiographically indeterminate. In a large study (Frankl 1988), mammography yielded a false positive rate of 48 percent, and is reported to be even less accurate in characterizing the dense breast tissue of younger women or tissue with fibro cystic disease (Ashley 1989; Robbins 1973). In screening situations, the false positive rate for x-ray mammography may be as high as 75–90 percent (Holmberg 1987). However, a number of large trials have shown that the positive predictive value for non-palpable breast cancer detected by mammography is disappointing. These trials reported that only 20–30% of non-palpable radiographically suspicious lesions are proven to be carcinoma by biopsy (Ciatto 1987, Hall 1988, Homer 1984, Meyer 1984, Rosenberg 1987, Holmberg 1987). In addition, many patients undergo prolonged follow-up with repeated mammograms and ultrasound for benign lesions. This was demonstrated in a large study, in which about 11% of the 34,282 women followed had lesions which were found to be benign. Clearly, mammography has a high rate of false positive diagnoses, leading to unnecessary biopsies, unnecessary careful follow-up of many patients over periods usually 2 year or more, undue psychological stress, inefficient patient management, and increased health care costs.

Improvements in the specificity of diagnosis (i.e. reduction in the false positive rate) would result in fewer unnecessary surgical biopsies performed, lower health care costs and better patient management. Development of noninvasive methods to further characterize indeterminate lesions demonstrated on mammography is therefore highly desirable. Adjunct imaging modalities have been shown to provide additional morphological and physiological information which cannot be obtained by mammography. Characterization of lesions using mammography in conjunction with ultrasound, for example, has been shown to be more accurate than diagnosis by mammography alone. This has particular application for women with dense breasts, where mammography has demonstrated a high rate of inaccuracy.

Therefore, there has been a long standing need to develop a percutaneous method of diagnosing breast diseases and which further allows for the treatment of the diseases to be performed percutaneously. Accordingly, the present inventors have determined that by employing three-dimensional ultrasonography in combination with two-dimensional imaging, breast lesions can be viewed in an entirely novel manner. The present invention preferably employs a three-dimensional imaging system as disclosed in U.S. Pat. No. 5,454,371 and U.S. patent application Ser. No. 08/562,590, filed Nov. 24, 1995, the contents of which are herein incorporated by reference. However, as will be understood by those of skill in the art, other three-dimensional ultrasonographic systems may be employed with the system and method of the present invention with similar success.

Further to this end, the majority of breast lesions operated on typically result in a scar and significant deformity to the patient. While some percutaneous biopsy techniques are presently in use, they are generally time consuming and tedious. It is believed that the system and method of the present invention will be quicker, provide greater accuracy and be significantly less damaging over conventional methods. Features of the present system include percutaneous access to lesions, rapid speed of performing the procedure, continuous feed-back relating to any complication that may occur, and increased flexibility in different approaches to be made to breast lesions.

SUMMARY OF THE INVENTION

It is an object of the present invention to provide a novel system and process for performing percutaneous medical procedures within the breast using three-dimensional ultrasonography which obviates or mitigates at least one of the disadvantages of the prior art.

According to one aspect of the present invention, there is provided a system for performing percutaneous medical procedures within a breast using ultrasonography comprising: a breast positioning means; a breast immobilization means; an ultrasonographic imaging means; a medical instrument positioning means; said breast immobilization means, said ultrasonographic imaging means and said medical instrument positioning means positioned in a known relationship relative to each other; said breast immobilization means being employed to immobilize the breast and a lesion contained therein for imaging by said ultrasonographic imaging means; and said ultrasonographic imaging means being employed to assist an operator in positioning said medical instrument positioning means relative to said lesion and guiding a medical instrument percutaneously to said lesion.

Preferably the percutaneous breast medical procedures may include cryosurgery, photodynamic therapy, hyperthermia, radiation seed implantation, and alcohol ablation or injection of tissue toxic substances.

Preferably, said percutaneous medical procedure is a biopsy procedure.

Also preferably, said ultrasonographic imaging means is a three-dimensional ultrasonographic imaging system with two dimensional imaging capabilities.

Also preferably, said ultrasonographic imaging means includes an articulated arm having an ultrasonographic transducer attached thereto, said articulated arm enabling movement of said ultrasonographic transducer in a plane parallel to said breast positioning means.

Also preferably, said ultrasonographic imaging system includes a drive means for moving said ultrasonographic transducer across said breast.

Also preferably, said drive means is a linear drive motor mounted to said ultrasonographic transducer.

Also preferably, said medical instrument positioning means is mounted on a track which permits motion in a plane parallel to said breast positioning means and guides said medical instrument into said lesion in a plane orthogonal to a scanning beam emitted from said ultrasonographic transducer.

According to another aspect of the present invention, there is provided a system for performing percutaneous biopsy within a breast using three-dimensional ultrasonography comprising: a breast positioning means; a breast immobilization means; an ultrasonographic imaging means; a biopsy instrument positioning means; said breast immobilization means, said three-dimensional ultrasonographic imaging means and said biopsy instrument positioning means positioned in a known relationship relative to each other; said breast immobilization means being employed to immobilize the breast and a lesion contained therein for imaging by said three-dimensional ultrasonographic imaging means; and said three-dimensional ultrasonographic imaging means being employed to assist an operator in positioning said biopsy instrument positioning means relative to said lesion and guiding a biopsy instrument percutaneously to said lesion.

According to another aspect of the present invention there is provided a process for performing percutaneous biopsy within a breast using three-dimensional ultrasonography comprising the steps of: i) positioning a breast with a breast positioning means; ii) obtaining an ultrasonographic image of said breast with an ultrasonographic imaging means to locate a lesion; iii) identifying said lesion and immobilizing said breast and said lesion with a breast immobilization means; iv) obtaining a three-dimensional image of said lesion with said ultrasonographic imaging means; v) with said three-dimensional image, positioning a biopsy instrument positioning means for guiding placement of a biopsy instrument in said lesion; vi) placing said biopsy instrument with said biopsy instrument positioning means percutaneously into said lesion under the guidance of subsequent ultrasonographic images; and vii) performing said breast biopsy with ultrasonographic images.

BRIEF DESCRIPTION OF THE DRAWINGS

A presently preferred embodiment of the present invention will now be described, by way of example only, with reference to the accompanying drawings, in which.

DETAILED DESCRIPTION OF THE PREFERRED EMBODIMENTS

Figure 1:
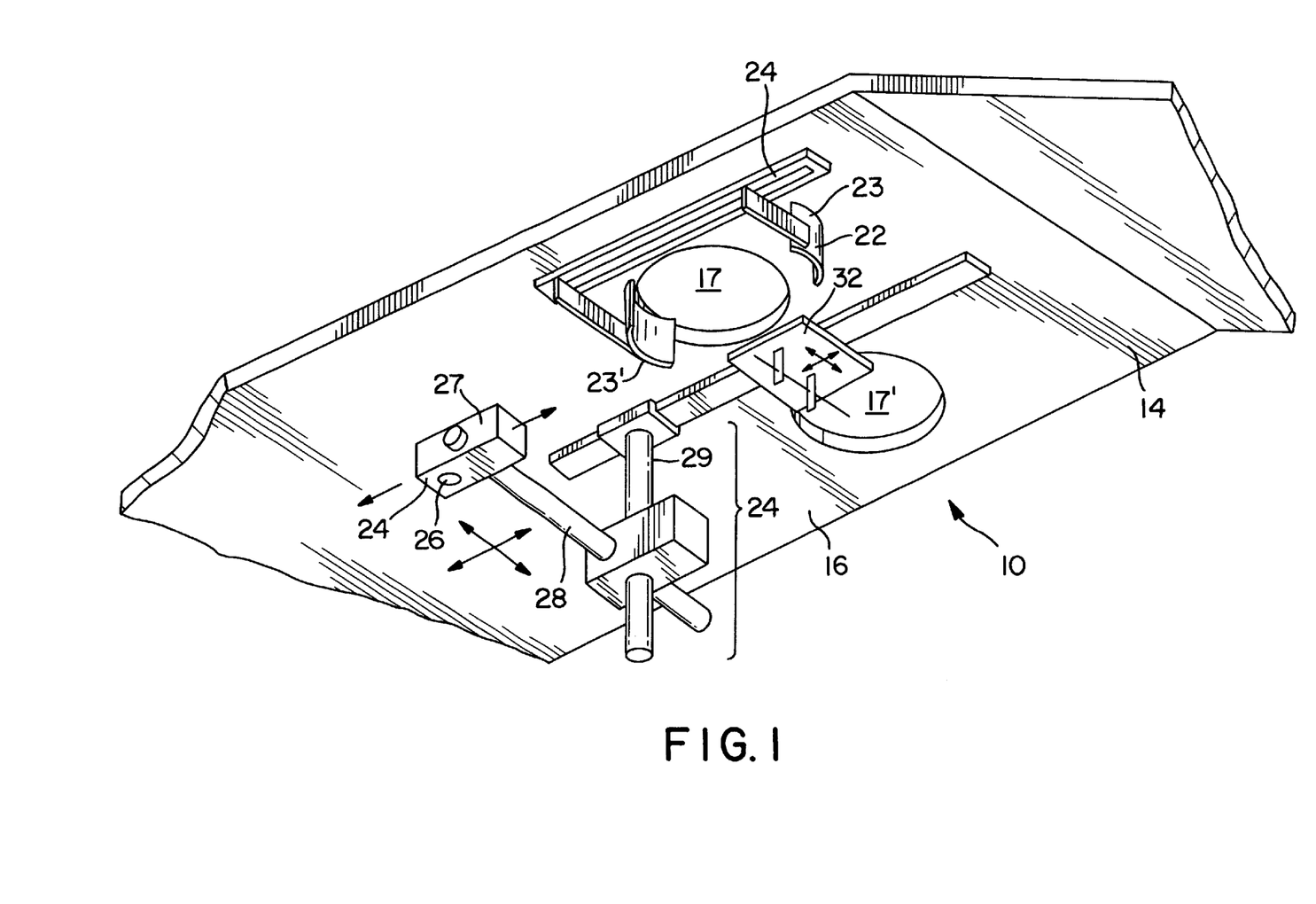
FIG. 1 shows a perspective view of a system for system for performing percutaneous medical procedures within a breast using ultrasonography in accordance with an embodiment of the present invention.

A system for performing percutaneous medical procedures within a breast using ultrasonography in accordance with an embodiment of the present invention is indicated generally at 10 in FIG. 1. System 10 generally comprises: a breast positioning means 14; a breast immobilization means 22, an ultrasonographic imaging means 24; and a biopsy instrument positioning means 32.

Figure 2A:
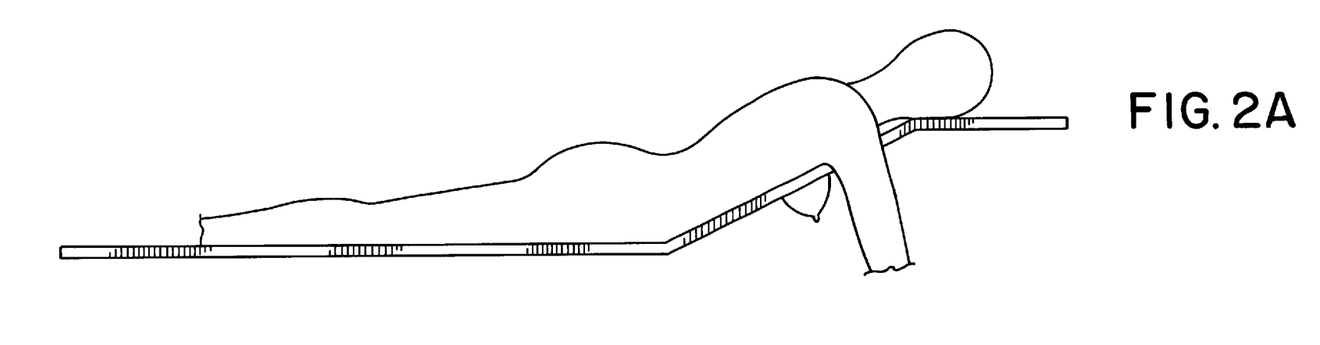
FIG. 2A shows an elevation view of a breast positioning means in accordance with the embodiment of FIG. 1.
Figure 2B:
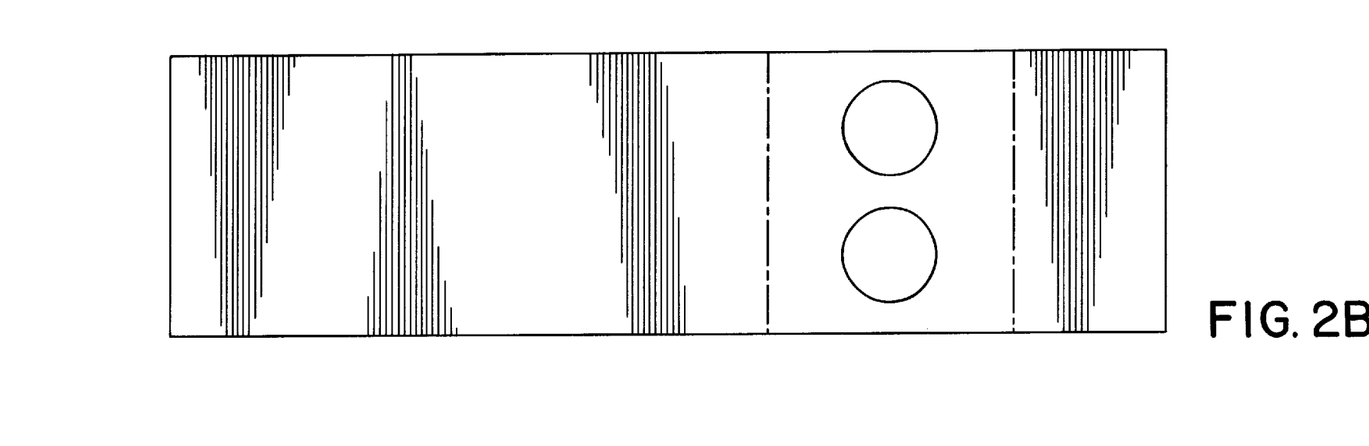
FIG. 2B shows a bottom view of the breast positioning means in accordance with the embodiment of FIG. 1.

The breast is a modified sweat gland located between the layers of the superficial fascia. Throughout most of its course it is directly beneath the subcutaneous tissue and easily accessible. There is a significant portion, however, that lies behind the anterior border of pectoralis major and extending into the axilla. In order to obtain access to virtually all of the breast tissue the present inventors have determined that the best patient position is a prone position with the breast lying dependent as indicated in FIG. 2. Preferably, the angle of the shoulder should be perpendicular to the torso with the elbows supported and not weight-bearing. In this position, pectoralis major and also pectoralis minor are relaxed allowing full access to the mammographic tissue.

Considering that the patient will preferably be prone or modified prone, there are at least two designs considered by the present inventors for breast positioning means 14. The first design, as shown in FIGS. 2A and 2B comprises a table formed from three portions. The first portion 15 is the longest and will be generally parallel to the floor and extend from the feet of the patient to approximately the level of the umbilicus. At this level there will be a second portion 16 joined to first portion 15 at an angle of approximately between 20° and 30°. This board will have two rounded apertures 17,17' within it to allow the patient's breasts to protrude in a dependent position. Each of these apertures will have a "trap-door" type arrangement (not shown) which will permit each breast to be pushed up out of the way when the trap-door is closed so that only one breast protrudes through at any one time. Having two breasts protruding through the table would generally interfere with access of the other apparatus required. A third portion 18 of table 14 is attached to second portion 16 at approximately the level of the shoulders and is generally horizontal. Portion 18 allows the patient to position her head comfortably during the procedure. Preferably, the width of the upper table should be no wider than the average female's shoulders as the shoulders are preferably positioned at approximately 90° to the torso.

Figure 3:
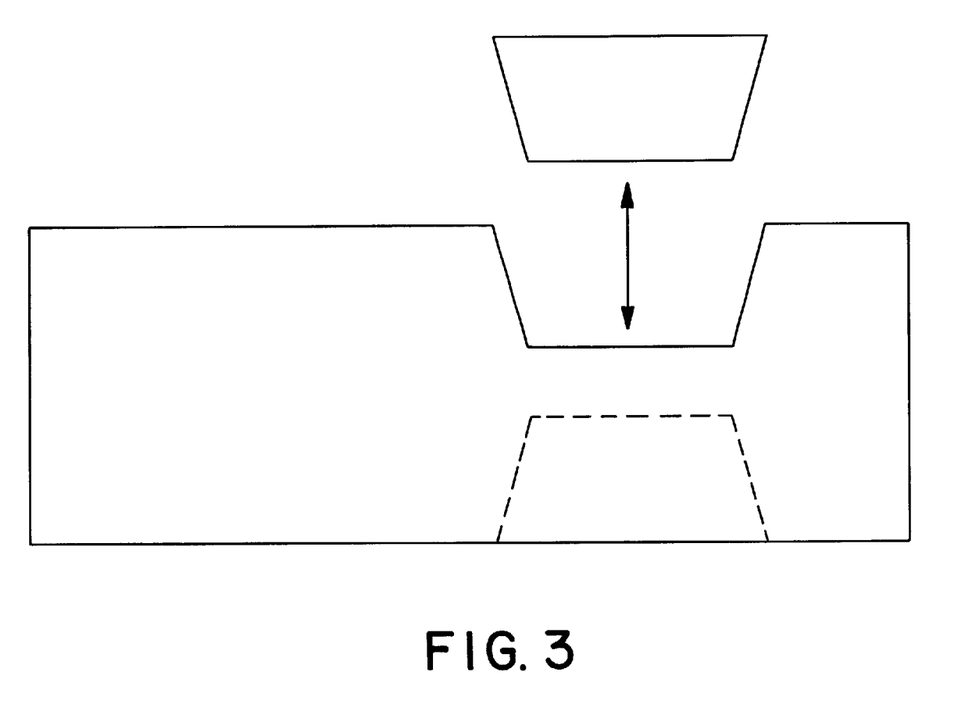
FIG. 3 shows a top view of an alternative breast positioning means in accordance with the present invention.
Figure 4A:
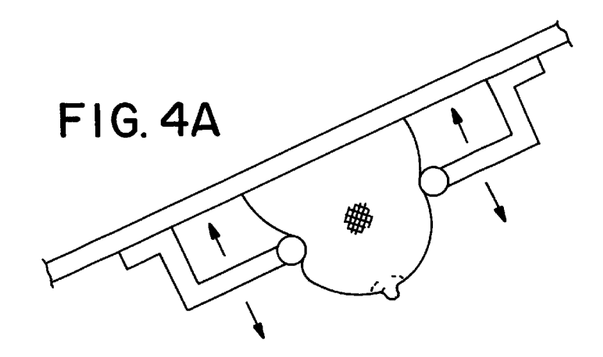
FIG. 4A shows the operation of a breast immobilization means in accordance with the embodiment of FIG. 1.
Figure 4B:
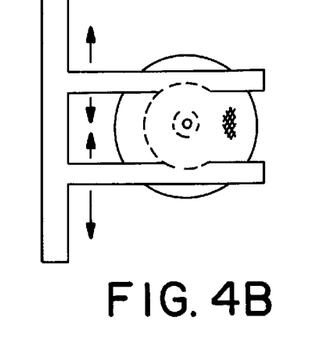
FIG. 4B shows the further operation of a breast immobilization means in accordance with the embodiment of FIG. 1.
Figure 4C:
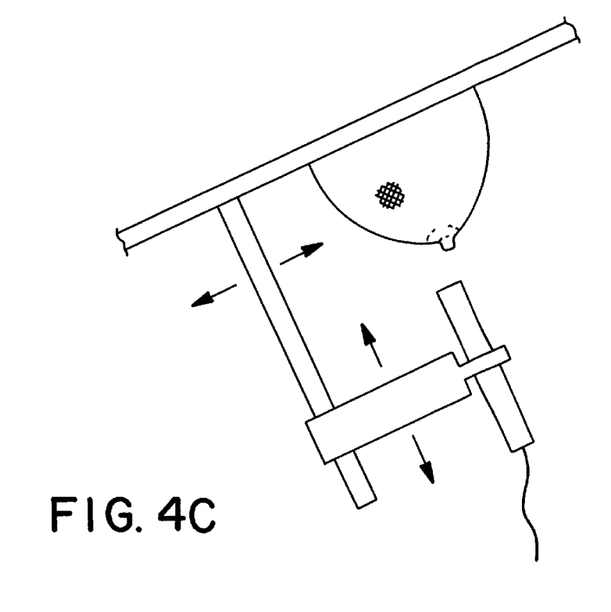
FIG. 4C shows the operation of an ultrasonograph imaging means in accordance with the embodiment of FIG. 1.
Figure 4D:
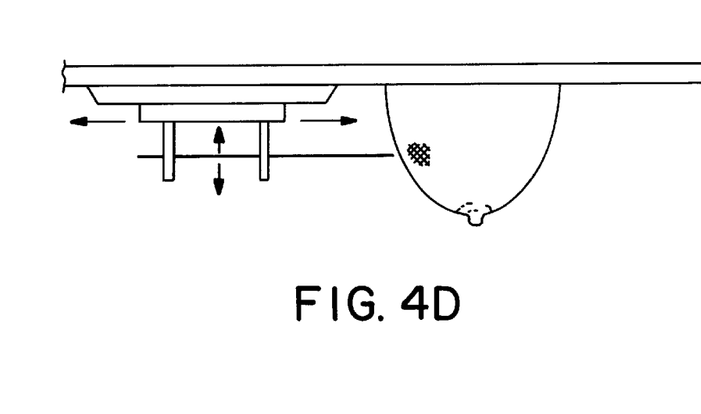
FIG. 4D shows the operation of a biopsy instrument positioning means in accordance with the embodiment of FIG. 1.

A second design for breast positioning means 14 is another table-type arrangement as shown in FIG. 3. In this embodiment, breast positioning means 14 is a generally key-shaped type arrangement where the entire torso of the patient is placed on a single flat board. The board narrows at the level of the breasts to allow support of the entire torso through direct pressure primarily on the sternum. With this arrangement a hinge-type or sliding gate member will be provided to allow the non-biopsied breast to be elevated out of the way.

Breast immobilization means 22 is employed for the following reasons: Firstly, many lumps within the breast are quite mobile and on trying to biopsy them, the lesion may move away from any needle; secondly, if the breast is compressed, a significant amount of normal tissue can be pressed out of the way so that only the suspicious area is biopsied with a minimum of other tissue around it; thirdly, the application of pressure decreases the risk of significant haematoma formation and fourthly, narrowing the amount of normal tissue between the transducer and the lesion improves ultrasonographic visibility.

Breast immobilization means 22 is preferably attached to the underside of table 14 but may also be mounted to the floor or a mounting plate parallel to the second portion of table 14 to make room for the other required equipment. A strong clamping mechanism that allows little to no motion of immobilization means is preferred. As shown schematically in the Figures, the device itself preferably comprises two soft curved pads 23,23'. Preferably pads 23,23' are made of a sterilizable material and will be non-allergenic. Pads 23,23' are then connected together by a sliding rod, track or rack and pinion type mechanism 24 and the like such that at least one of the pads 23,23' is movable for compressing and immobilizing the breast. Movement of the at least one pad 23,23' can either be by hand or by mechanical means such as a linear motor, hydraulic actuator or other suitable type mechanism similar to the mechanisms presently employed on a conventional mammographic table. It is contemplated that the selection of an appropriate device would be apparent to one of skill in the art. Preferably, breast immobilization means 22 is mountable to table 14 in any direction so as not to interfere with the other required equipment. Lesions generally occur in the upper-outer quadrant but can occur in any quadrant and the actual location of the area of the breast being compressed will be dependent on where the suspicious area is.

Ultrasonographic imaging means 24 includes several components preferably including a three-dimensional imaging system with dedicated graphics software and a graphical user interface. An ultrasonographic transducer 26 will be positioned in a scanning mechanism housing 27 as previously described in the previously incorporated by reference patent and patent application. The housing is attached to the table using two articulated arms 28 and 29 which are employed to position the transducer over the breast. Arms 28 and 29 will allow movement in a plane parallel to the second portion of table 14 (two perpendicular directions both of which will be parallel to the table surface). This will allow the entire device to be suspended from breast positioning means 14, floor or other suitable surface but enable the entire breast to be scanned. The direction of scanning will be in an anteroposterior direction through the breast.

A biopsy instrument positioning means 32 is also be attached to table 14 and is positioned in such a manner such that the relative position between positioning means 32 and ultrasonographic imaging means 24 is known and referenceable. Positioning means 32 includes a split ring type biopsy instrument guide or a 270 degree split cylinder for holding and guiding the medical instrument.

The modes of operation, and specifically the degrees of movement, of the breast immobilization means, the biopsy instrument positioning means and the ultrasonographic imaging means are shown schematically in FIGS. 4A, 4B, 4C and 4D respectively.

Figure 5A:
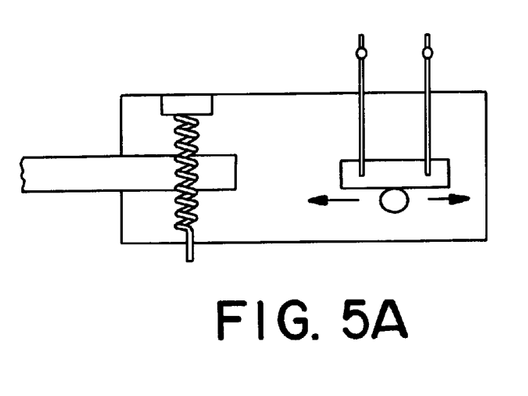
FIGS. 5A–5E are schematic representations of a split-ring type biopsy instrument guide in accordance with one embodiment of the present invention.
Figure 5B:
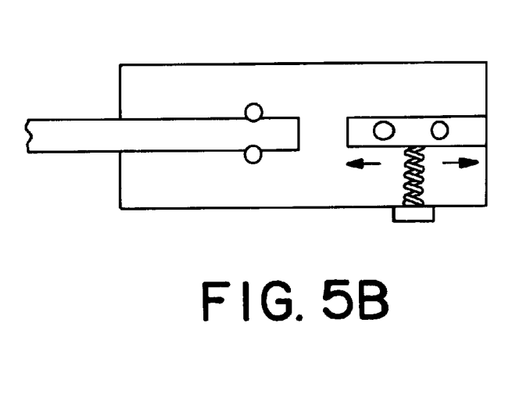
Figure 5C:
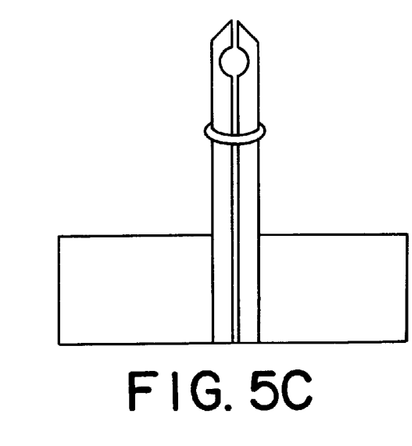
Figure 5D:
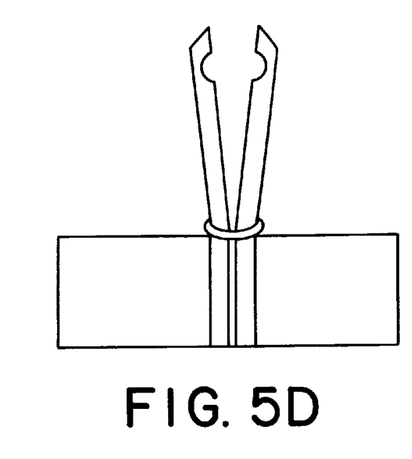
Figure 5E:
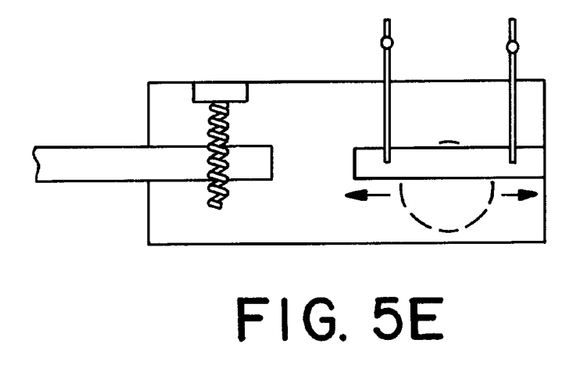

The split ring type biopsy instrument guide is shown schematically in FIGS. 5A–5E. The guide comprises a pair of elongate clamps provided with an aperture adapted to receive a biopsy instrument. Each clamp has an open position and a closed position, as shown in FIGS. 5E and 5D, respectively. The clamp is maintained in its closed position by means of a circular band which, when proximal the aperture, prevents the two halves of the clamp from opening.

Figure 6A:
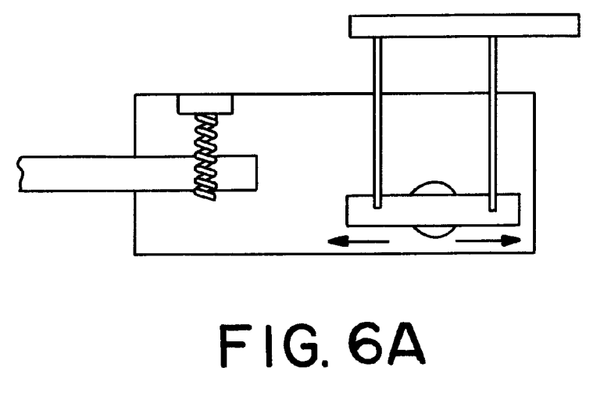
FIGS. 6A–6C are schematic representations of a split-cylinder type biopsy instrument guide in accordance with a second embodiment of the present invention.
Figure 6B:
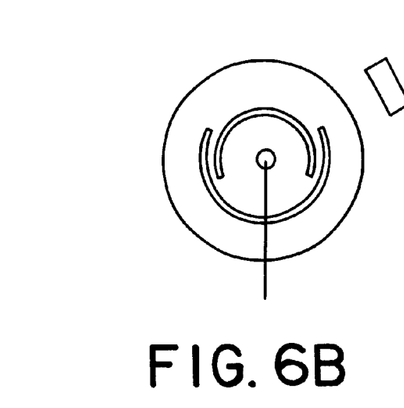
Figure 6C:
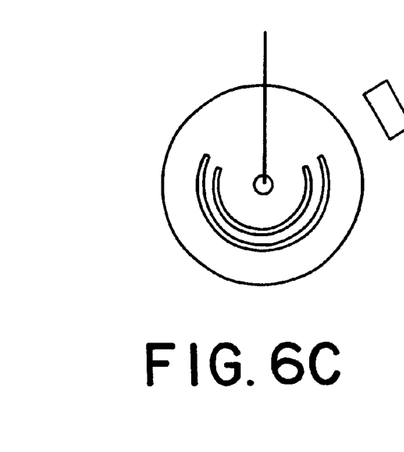

The split cylinder type biopsy instrument guide is shown schematically in FIGS. 6A–6C. The guide comprises a pair of complementary quonset-shaped holders, a first one of which is fixed with respect to a positioning track. The second holder is rotatable with respect to the first holder around the longitudinal axis of the first holder. The second holder is rotatable from a closed position shown in FIG. 6B to an open position shown in FIG. 6C. A biopsy instrument which is inserted along the length of the first holder when open, is retained within the guide when the second holder is rotated to the closed position. The biopsy instrument is effectively clamped in a known orientation with respect to the positioning track.

The process for preparing the patient for the biopsy and obtaining an ultrasonographic image for the purposes of determining biopsy instrument positioning will now be described. It is contemplated that the lesion will first be localized either clinically or with two-dimensional ultrasonography or mammography prior to commencing the procedure. Immediately prior to starting the procedure the lesion will be scanned to assess its ultrasonographic visibility. As shown in FIG. 2A, the patient is positioned prone on breast positioning means 14 with the affected breast left in the dependent position through one of apertures 17,17'. The pectoralis major muscle relaxed in the manner previously described. Ultrasonographic transducer 26 is mounted in the housing 25. The breast is then wiped with alcohol and transducer 26 is then positioned up against the breast. The Time Gain Compensation (TGC) curve of the associated ultrasound machine of ultrasonographic imaging means 24 will be optimized to show the lesion. Transducer 26 will then be moved to the mid-portion of the motorized housing and the centre of the lesion will be lined up by watching the image on a monitor. Once this is done transducer 26 is moved within the housing to one end of its travel. On activation, all or a portion of the breast will be scanned. It should be noted that while it may be possible to scan the breast manually, the present inventors have determined that the best results are obtained when transducer 26 is attached to a drive actuated housing wherein the rate of the scan is controlled and extraneous movement is minimized. Further to this end, while it is presently contemplated that movement of transducer 26 is accomplished a linear drive mechanism within the housing, it is further contemplated that similar scanning results may be obtained moving transducer 26 in a tilted or rotational manner.

In some patients it may be necessary to apply some surgical tape directly to the breast to flatten it out to allow ease of contact with the transducer. It is envisaged that this will not happen very often.

A three-dimensional scan is then obtained and a three-dimensional volume image is constructed, viewed and checked to ensure that the lesion is in proper position.

The next step will involve application of breast immobilization means 22 to the breast in the vicinity of the lesion. The lesion will be compressed in a direction approximately perpendicular to the ultrasound beam. Preferably, an attempt should be made to force the lesion closer to the skin surface, i.e., closer to transducer 26. Once this has been done, the step previously described for performing a three-dimensional ultrasonographic scan will be repeated.

Once the three-dimensional scan has been completed, the software as described in the patent and patent application previously described as being incorporated herein by reference is applied to the three-dimensional volume and the lesions is then viewed and/or manipulated in three-dimensions. Suitable positions for acquiring the biopsies or positioning the needle will be planned out. This information will be conveyed initially by hand to the needle position located at 90° to the ultrasonographic transducer 26. With this information, biopsy instrument positioning means 32 will be positioned and a needle will subsequently be positioned manually.

It is further contemplated that direct computer feed-back of the needle position could be employed to automatically position the needle and a further refinement will be the application of robotics to not only reposition the needle positioned, but also to position the needle exactly within the affected area.

The insertion of the needle into the lesion will be done under direct guidance wherein the needle is imaged using conventional two-dimensional ultrasonography or three-dimensional ultrasonography. It is important to note that for optimal imaging and guidance, the needle should be inserted parallel to the long axis of the ultrasound transducer 26 or approximately perpendicular to the scanning plane.

While the present procedure has been described with respect to breast biopsy, other possible percutaneous breast medical procedures may include cryosurgery, photodynamic therapy, hyperthermia, radiation seed implantation, and alcohol ablation or injection of tissue toxic substances. These procedures may be performed using the system of the resent invention with minimal modification which would be apparent to those of skill in the art.

The present invention has been described with reference to a presently preferred embodiment. Other variations and embodiments of the present invention may be apparent to those of ordinary skill in the art. Accordingly, the scope of protection sought for the present invention is only limited as set out in the attached claims.

What is claimed is:

1. A system for performing percutaneous medical procedures within a breast using ultrasonography comprising:
    a breast positioning means;
    a breast immobilization means;
    an ultrasonographic imaging means;
    a medical instrument positioning means;
    said breast immobilization means, said ultrasonographic imaging means and said medical instrument positioning means positioned in a known relationship relative to each other;
    said breast immobilization means being employed to immobilize the breast and a lesion contained therein for imaging by said ultrasonographic imaging means; and
    said ultrasonographic imaging means being employed to assist an operator in positioning said medical instrument positioning means relative to said lesion and guiding a medical instrument percutaneously to said lesion and wherein said ultrasonographic imaging means is a three-dimensional ultrasonographic imaging system with two dimensional imaging capabilities.

2. The system according to claim 1 wherein said medical procedure is a biopsy procedure.

3. The system according to claim 1 wherein said ultrasonographic imaging means includes an articulated arm having an ultrasonographic transducer attached thereto, said articulated arm enabling movement of said ultrasonographic transducer in a plane parallel to said breast positioning means.

4. The system according to claim 3 wherein said ultrasonographic imaging system includes a drive means for moving said ultrasonographic transducer to obtain a breast ultrasonographic scan.

5. The system according to claim 4 wherein said drive means is a linear drive motor mounted to said ultrasonographic transducer.

6. The system according to claim 1 wherein, said medical instrument positioning means is mounted on a track which permits motion in a plane parallel to said breast positioning means and guides said medical instrument into said lesion in a plane orthogonal to a scanning beam emitted from said ultrasonographic transducer.

7. A system for performing percutaneous biopsy within a breast using three-dimensional ultrasonography comprising:
    a breast positioning means;
    a breast immobilization means;
    an ultrasonographic imaging means;
    a biopsy instrument positioning means;
    said breast immobilization means, said ultrasonographic imaging means and said medical instrument positioning means positioned in a known relationship relative to each other;
    said breast immobilization means being employed to immobilize the breast and a lesion contained therein for imaging by said ultrasonographic imaging means; and
    said ultrasonographic imaging means being employed to assist an operator in positioning said medical instrument positioning means relative to said lesion and guiding a biopsy instrument percutaneously to said lesion.

8. The system according to claim 7 wherein said ultrasonographic imaging means is provided with two-dimensional imaging capabilities.

9. The system according to claim 8 wherein said ultrasonographic imaging means includes an articulated arm having an ultrasonographic transducer attached thereto, said articulated arm enabling movement of said ultrasonographic transducer in a plane parallel to said breast positioning means.

10. The system according to claim 9 wherein said ultrasonographic imaging system includes a drive means for moving said ultrasonographic transducer to obtain a breast scan.

11. The system according to claim 10 wherein said drive means is a linear drive motor mounted to said ultrasonographic transducer.

12. The system according to claim 7 wherein, said biopsy instrument positioning means is mounted on a track which permits motion in a plane parallel to said breast positioning means and guides said biopsy instrument into said lesion in a plane orthogonal to a scanning beam emitted from said ultrasonographic transducer.

13. A process for performing percutaneous biopsy within a breast using three-dimensional ultrasonography comprising the steps of:

i) positioning a breast with a breast positioning means;

ii) obtaining an ultrasonographic image of said breast with an ultrasonographic imaging means to locate a lesion;

iii) identifying said lesion and immobilizing said breast and said lesion with a breast immobilization means;

iv) obtaining a three-dimensional image of said lesion with said ultrasonographic imaging means;

v) with said three-dimensional image, positioning a biopsy instrument positioning means for guiding placement of a biopsy instrument in said lesion;

vi) placing said biopsy instrument with said biopsy instrument positioning means percutaneously into said lesion under the guidance of subsequent ultrasonographic images; and vii) performing said breast biopsy with ultrasonographic images.

* * * * *